US009808321B2

(12) United States Patent
Huldin et al.

(10) Patent No.: US 9,808,321 B2
(45) Date of Patent: Nov. 7, 2017

(54) DYNAMIC REFERENCE FRAME FOR SURGICAL NAVIGATION SYSTEM

(71) Applicant: IZI MEDICAL PRODUCTS, LLC, Owings Mills, MD (US)

(72) Inventors: Nelson L. Huldin, Alexandria, VA (US); Greg Groenke, Owings Mills, MD (US); Holger-Claus Rossner, Feldkirchen B. Muenchen (DE)

(73) Assignee: IZI Medical Products, LLC, Owing Mills, MD (US)

( * ) Notice: Subject to any disclaimer, the term of this patent is extended or adjusted under 35 U.S.C. 154(b) by 164 days.

(21) Appl. No.: 14/807,914

(22) Filed: Jul. 24, 2015

(65) Prior Publication Data

US 2017/0020621 A1 Jan. 26, 2017

(51) Int. Cl.
A61B 19/00 (2006.01)
A61B 90/10 (2016.01)
A61B 34/20 (2016.01)
A61B 90/00 (2016.01)
A61B 17/00 (2006.01)

(52) U.S. Cl.
CPC .............. *A61B 90/10* (2016.02); *A61B 34/20* (2016.02); *A61B 90/39* (2016.02); *A61B 2017/0023* (2013.01); *A61B 2017/00199* (2013.01); *A61B 2017/00526* (2013.01); *A61B 2034/2055* (2016.02); *A61B 2034/2068* (2016.02); *A61B 2090/3937* (2016.02); *A61B 2090/3983* (2016.02)

(58) Field of Classification Search
CPC ......... A61B 90/10; A61B 90/39; A61B 34/20; A61B 2090/3983; A61B 2090/3937; A61B 2017/00199; A61B 2017/00526; A61B 2017/0023; A61B 2034/2055; A61B 2034/2068
USPC ....................................................... 606/130
See application file for complete search history.

(56) References Cited

U.S. PATENT DOCUMENTS 6,273,896 B1 * 8/2001 Franck ................... A61B 90/10
606/130
6,560,354 B1 5/2003 Maurer, Jr. et al.
7,072,707 B2 7/2006 Galloway, Jr. et al.
(Continued)

FOREIGN PATENT DOCUMENTS

DE 69833881 T2 12/2006
DE 602004004158 T2 10/2007
(Continued)

OTHER PUBLICATIONS

International Search Report and Written Opinion dated May 4, 2016 in corresponding International Application No. PCT/IB2015/055674.

*Primary Examiner* — Diane Yabut
*Assistant Examiner* — Martin T Ton
(74) *Attorney, Agent, or Firm* — Ajay A. Jagtiani; Miles & Stockbridge P.C.

(57) ABSTRACT

A device and manufacturing method for a surgical navigation system, comprising a rigid frame member having a top portion, a plurality of mounts each having a top surface, wherein the plurality of mounts are disposed at prescribed locations of the top portion. The top surface of the plurality of mounts are configured to align on a common horizontal plane that extends in parallel with the top portion of the frame member.

37 Claims, 5 Drawing Sheets

(56) References Cited

U.S. PATENT DOCUMENTS

| | | | | |
|---|---|---|---|---|
| 7,725,162 | B2* | 5/2010 | Malackowski | A61B 90/36 |
| | | | | 600/424 |
| 7,840,256 | B2 | 11/2010 | Lakin et al. | |
| 7,881,770 | B2 | 2/2011 | Melkent et al. | |
| 8,073,530 | B2 | 12/2011 | Solar et al. | |
| 8,548,563 | B2 | 10/2013 | Simon et al. | |
| 2004/0116802 | A1 | 6/2004 | Jessop et al. | |
| 2012/0201421 | A1 | 8/2012 | Hartmann et al. | |
| 2013/0096570 | A1* | 4/2013 | Solar | A61B 90/11 |
| | | | | 606/108 |

FOREIGN PATENT DOCUMENTS

| | | |
|---|---|---|
| DE | 102009019986 A1 | 11/2010 |
| DE | 102010060914 A1 | 5/2012 |
| DE | 102011054730 A1 | 4/2013 |
| WO | 2006012491 A1 | 2/2006 |

\* cited by examiner

DYNAMIC REFERENCE FRAME FOR SURGICAL NAVIGATION SYSTEM

BACKGROUND

Field of the Invention

The present invention relates generally to surgical navigation systems. More particularly, the present invention relates to a referencing device for a surgical navigation system.

Related Art

Surgical navigation systems are employed in a variety of surgical applications, for example, in neurosurgery, oral, maxillofacial and facial surgery, ear nose and throat (ENT) surgery or also for limb implantation in orthopedic surgery. Based on three-dimensional patient image data, which are obtained by means of X-ray images, computer tomography (CT), magnetic resonance tomography (MRT) and/or positron emission tomography (PET), surgical navigation systems of this type enable the position of medical instruments to be visualized in real-time in the patient image data in order to thereby assist the surgeon during operable procedures.

To this end, it may be necessary to record and monitor the position and orientation of the patient or a specific body part on which a surgical procedure is to be carried out—also referred to as "tracking." Conventional referencing devices, employed within such surgical navigation systems, for example, have been used usually comprising reference frames to which marking elements such as light-reflecting spherical markers are attached. The light-reflecting spherical markers allow a stereo camera system of the navigation system to record the precise position and orientation of the referencing device.

It is, therefore, an object of the present invention to overcome the deficiencies of the prior art to provide an improved apparatus capable of providing increased range of motion in at least multiple to an infinite amount of directions while more easily achieving and maintaining a sterile operating environment. It is a further goal of the present invention to provide a method and apparatus that achieves and maintains a dependable fixed position of the referencing device during operational procedures that eliminates the need to recalibrate the system.

SUMMARY

The foregoing needs are met, to a great extent, by the present invention, wherein in one aspect a device is provided that in some embodiments comprises a rigid frame member having a top portion, a plurality of mounts each having a top surface, wherein the plurality of mounts are disposed at prescribed locations of the top portion. The top surface of the plurality of mounts are configured to align on a common horizontal plane that extends in parallel with the top portion of the frame member.

In accordance with another embodiment of the present invention, a method is provided that in some embodiments comprises connecting a plurality of mounts on a top surface of a frame member, wherein each plurality of mounts has a top surface. The top surface of the plurality of mounts are configured to align on a common horizontal plane that extends in parallel with the top surface of the frame member. The method may also include mounting one or more tracking marker elements on each mount and aligning a centerline of each tracking marker element with the top surface.

There has thus been outlined, rather broadly, certain embodiments of the invention in order that the detailed description of the invention herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the concept upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Still other aspects, features and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Definitions

Figure 1:
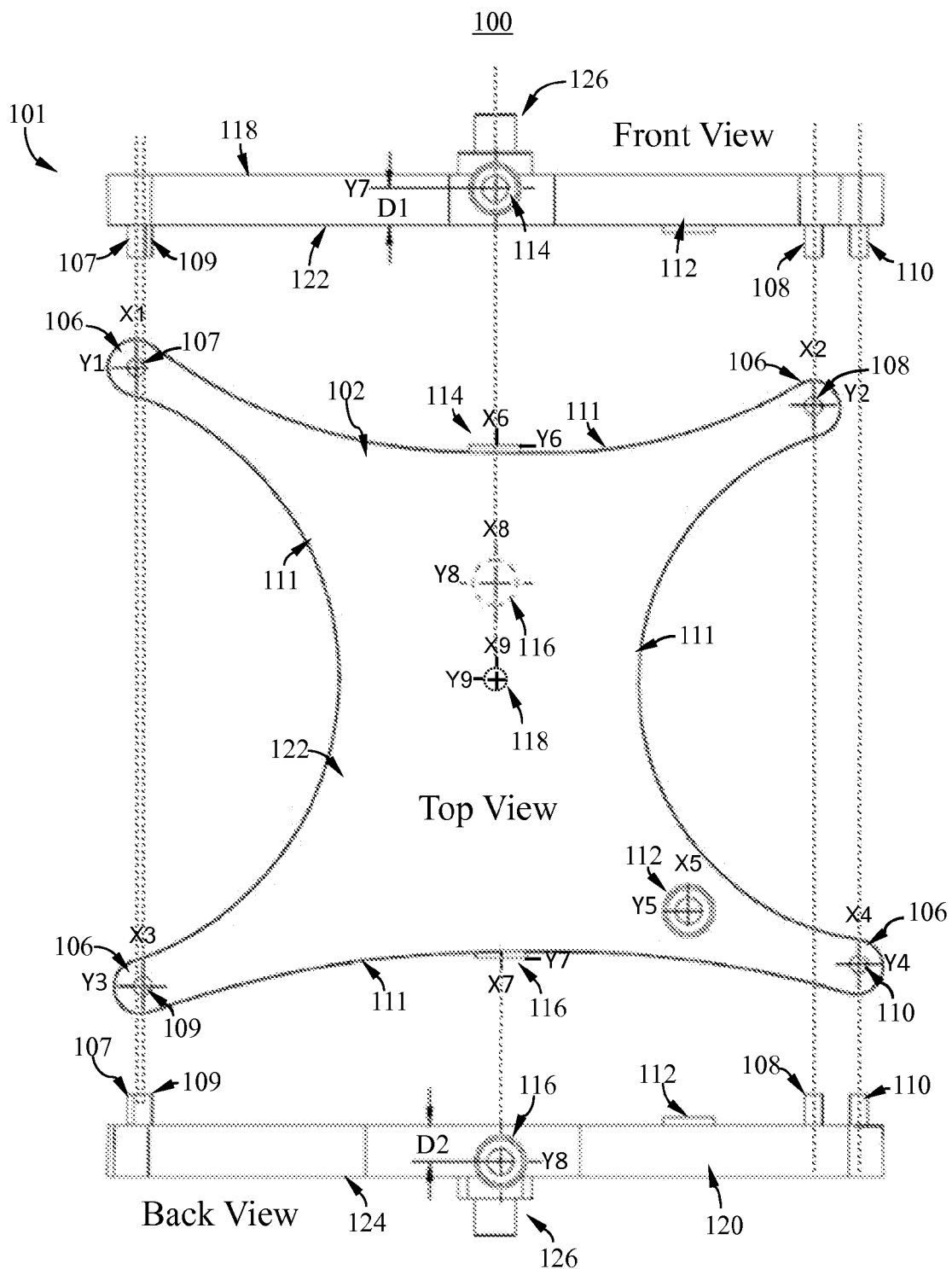
FIG. 1 illustrates a top view, front view and back view of a disposable dynamic reference for surgical navigation system, according to an embodiment of the present invention.

Where the definition of terms departs from the commonly used meaning of the term, applicant intends to utilize the definitions provided below, unless specifically indicated.

For the purposes of the present invention, directional terms such as "top", "bottom", "upper", "lower", "above", "below", "left", "right", "horizontal", "vertical", "upward", "downward", etc., are merely used for convenience in describing the various embodiments of the present invention.

For purposes of the present invention, the term "astroid" refers to a geometric design of a hypocycloid with four concave (inwardly-curved) sides which may include a variety of names, including tetracuspid, cubocycloid, and paracycle.

For purposes of the present invention, the term "cusp" refers to a point made by the intersection of two curved lines or curved structures. In select disclosed embodiments, the point may be rounded For purposes of the present invention, the term "disposable" refers intended to be used once, or until no longer useful, and then discarded.

For purposes of the present invention, the term "trapezium" refers to a geometric design of trapezoid with no parallel sides.

For purposes of the present invention, the term "indicia" refers distinctive marks, characteristic markers or indications.

For purposes of the present invention, the term "patient space" refers to the physical space within which a patience exists or is immersed. The physical space can include any portion or the entire patient or area surrounding the patient including navigation space of all physical entities such as interventional or surgical instruments or tracking makers that may interact with the patient. Generally patient space includes that area which is part of the navigable field in which an instrument or navigated portion can be tracked.

For purposes of the present invention, the term "registering" refers to a process for determining the geometric relationship between an anatomic structure(s) of interest and a 3-dimensional (3D) computer image constructed, for example, from the preoperative CT scan. By way of this registration, a correct, spatial reference between the 3D image data and the position and orientation of the body part of the patient, observed by means of referencing device, can be produced.

For purposes of the present invention, the term "surgical navigation" refers to computer assisted surgery (CAS) representing a surgical concept and set of methods that use computer technology for pre-surgical planning and for guiding or performing surgical interventions. CAS is also known as computer aided surgery, computer assisted intervention, image guided surgery and surgical navigation.

For purposes of the present invention, the term "surgical navigation system" refers a system that allows visualization of an operative site and surgical instruments simultaneously and relates them to the patient's diagnostic images (e.g., computed tomographic (CT) scans and magnetic resonance imaging (MRI)). A surgical navigation system is used to guide the surgeon's movements during an operation. It may display the real-time position of each instrument and anatomical structure. These systems are used in orthopedics, ENT, neurology and other surgical specialties. Real-time observations occur via MRI, scanner, video camera or another imaging process. Navigation data are incorporated into the image to help the surgeon determine precise position within the organism. Medical imaging is sometimes used to plan an operation before surgery. Data integration enables the system to compare the actual position of the target object with the ideal location established during the planning phase. Such systems may be mechanical, electromagnetic or optical. The most common are optical devices, either passive or active. In the former, cameras locate specific markers such as reflective targets, particular shapes or colors. Active systems locate LEDs.

For purposes of the present invention, the term "touch" or "touched" refers to action or condition of interacting with a target using any appropriate means to include bodily appendage such as fingers or any other part of the body or any other mechanical or electrical tool or device.

For purposes of the present invention, the term "x-direction" refers to the direction aligned with the x-axis of a coordinate system.

For purposes of the present invention, the term "y-direction" refers to the direction aligned with the y-axis of a coordinate system.

For purposes of the present invention, the term "z-direction" refers to the direction aligned with the z-axis of a coordinate system.

Description

The invention will now be described with reference to the drawing figures, in which like reference numerals refer to like parts throughout. The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Conventional navigation systems and/or referencing devices are known, for example, from documents DE 10 2011 054 730 A1, DE 698 33 881 T2, DE 10 2010 060 914 A1 or DE 60 2004 004 158 T2. WO 2006/012491 discloses marker elements together with a unit carrying the marker elements—referred to as reference frames—as a single disposable unit which can be produced by injection molding. However, traditional navigation systems do not always allow for the desired positioning and orientation of the referencing device, for example, due to structural limitations in the design of its arranged configuration and/or restrictions in movement such as limited multiple ranges of motion and/or operating degrees of freedom.

Another concern may include operating and maintaining a sterile environment during surgical procedures. Medical devices, such as referencing devices must also be sterile. Within such an environment, marker elements may be removably attached, for example, by means of a standardized clip attachment to pins arranged on the referencing device. The referencing device may thus be sterilized without marker elements and new, sterile, disposable marker elements may be utilized for each use. Conventional corresponding marker elements are known, for example, from document DE 10 2009 019 986 A1.

In order to deduce the position and orientation of a patient (or as the case may be, the body part of a patient on which a surgical procedure is to take place), and in order to produce a correct reference to the 3D image data, it is necessary to calibrate the surgical navigation system by executing a registration step. Various reference points are thereby successively localized on the patient using a navigation apparatus and correlated with corresponding points in the 3D image data.

The registration process determines the geometric relationship between the anatomic structures of interest and the 3-dimensional (3D) computer image constructed, for example, from the preoperative CT scan. Registration involves two steps. First, the reference sensor is secured to a non-mobile structure. Then, a registration tip, for example, is used sequentially to touch pre-selected registration points (e.g., fiducial markers). Registration points may be any anatomic structures that are recognizable on the preoperative image (e.g. teeth, skin and bone). Each time a registration point is touched with the registration tip, the computer records the location of the position sensor and the reference sensor. Using, for example, at least three registration points, the computer calculates the physical position of the anatomic structure with respect to the reference sensors. The computer then uses this registration information to measure the position of the pencil relative to the preoperative CT scan. The patient's body part can be mobilized freely without the need to re-initialize the registration process, because the reference sensor is rigidly attached to the relevant structure of the patient. By way of this registration, a correct, spatial reference between the 3D image data and the position and orientation of the body part of the patient can be produced.

In particular, in the case of surgical procedures involving the brain, it is usually not possible to simply be limited to reference points in the operating area for a necessarily precise registration, but rather it is necessary, in the vast majority of cases, to select a plurality of reference points at different locations on the body of the patient. Since for this purpose unhindered access to these locations on the body of the patient is necessary, registration must thus take place before the patient can be finally prepared for the actual surgical procedure and covered in a sterile manner in the areas outside of the operating area.

As a practical matter, and as it pertains to the registration device itself, following a successful registration procedure necessarily means the registration device must be considered as being potentially contaminated. Thus, appropriate measures for protecting the patient must be taken before the image-guided surgical procedure using the navigation system can take place. As such, the reference frame is thus usually detached from the fixation unit, sterilized, and provided with new sterile marker elements and reconnected to the fixation unit. The fixation unit as well as the interface between the fixation unit and the reference frame must next be draped and/or otherwise covered. To achieve this, holes are typically generated in medical drapes in order to allow the reference frame or its components to protrude therethrough and to subsequently attach to the fixation unit. Additional care to secure and maintain medical drapes is also provided in order to achieve a covering considered at least sufficiently secure. From a user perspective, this approach is presented as less than desirable since, on the one hand, the effort is labor intensive and significant staff effort is required in order to provide the necessary draping and covering for operational procedure. And, on the other hand, the draping and covering is often regarding as insufficiently secure for operating procedures. This risks the sterility of the operating environment and loss of time in addressing the same.

Accordingly, it is, therefore, an object of the present invention to overcome the deficiencies of the prior art to provide an improved apparatus capable of providing increased range of motion in at least multiple to an infinite amount of directions while more easily achieving and maintaining a sterile operating environment. It is a further goal of the present invention to provide a method and apparatus that achieves and maintains a dependable fixed position of the referencing device during operational procedures that eliminates the need to recalibrate the system.

Embodiments of the present invention disclose the design and use of a disposable, single-use medical device. Turning to device representation 100 in FIG. 1, a disposable Dynamic Reference Frame (DRF) 101 for use in a surgical navigation system is illustrated. The dynamic reference frame comprises a track-able top portion 102 for positioning and mounting one or more tracking marker elements 106 onto one or more mounting posts 107, 108, 109 and 110 disposed, for example, at four endpoints of the astroid design.

In the disclosed embodiment, DRF 101 has substantially an asteroid design. One disclosed design includes an external contour having an asymmetrical configuration that has been rotated by approximately ⅛ of a turn about its central normal axis (a rotation angle in the range of 22 degrees to 23 degrees) having, for example, four concave (inwardly-curved) sides 111. Select embodiments may include concave (inwardly-curved) sides 111 generally terminating with rounded corners (cusps 113) where two concave (inwardly-curved) sides meet. While four exemplary structural concave (inwardly-curved) sides 111 are shown for illustrative purposes, one skilled in the art will readily appreciate more or fewer concave (inwardly-curved) sides may be employed by disclosed embodiments. One or more tracking marker elements 106 are mounted onto one or more mounting posts 107, 108, 109 and 110 disposed, for example, at the intersection points of the concave (inwardly-curved) sides 111. In the exemplary structure DRF 101, one or more tracking marker elements 106 are mounted onto one or more mounting posts 107 disposed at the rounded corners (cusps 113) connecting the four concave (inwardly-curved) sides 111.

If the dynamic reference frame 100 is used as a fiducial marker, the dynamic reference frame 100 may further comprise one or more localization divots such as, for example, divots 112 disposed at the top portion 102 of the exemplary DRF 101, illustrated in FIG. 1. Localization divots disposed on DRF 101 allow a pointer probe or any appropriate mechanism to determine the location of DRF 101 relative to the patient by engaging one or more divots in a selected manner in patient space. In this way, a navigation system comprising DRF 101 is able to determine the position of the DRF 101 relative to the patient. Furthermore, one or more localization divots 112 may be pointed out in the pre-acquired radiological patient image in order to register the image space with the patient space. In this way detected movement of the DRF 101 may be used to determine movement of the patient. It will be understood that the one or more localization divots may be positioned in any appropriate portion of DRF 101 but are generally provided in an easily accessible and viewable area. Moreover, there may be multiple divots 112 or landmarks, as discussed herein. The multiple divots 112 may be used as fiducial markers. DRF 101 may also include a radio-opaque material to be imaged in various imaging techniques.

The location of the localization divots and mounting posts for mounting the one or more tracking marker elements are denoted by their respective x and y coordinates in the patient space. Taking mounting post 107 as the origin point, parameters X1 and Y1 may represent the two dimensional 0,0 coordinate values, respectively, in patient space. In the exemplary embodiment of FIG. 1, two-dimensional coordinate values of mounting post 108 for mounting tracking marker 106, denoted in FIG. 1 as X2 and Y2, may be selected from an applicable range approximately spanning from 4.722 to 4.732 and 0.258 to 0.268 inches, respectively. In accordance to one exemplary embodiment, parameters X2 and Y2 may be set to an optimal value of approximately 4.727 and 0.263 inches, respectively. Parameters X3 and Y3, denoted in FIG. 1, represent the two-dimensional spatial coordinates of mounting post 109. In the exemplary embodiment of FIG. 1, spatial coordinated X3 and Y3 may be selected from an applicable range approximately spanning from 0.042 to 0.052 inches and 4.248 to 4.258 inches, respectively. In accordance to one exemplary embodiment, parameters X3 and Y3 may be set to an optimal value of approximately 0.047 and 4.253 inches, respectively. Parameters X4 and Y4, denoted in FIG. 1, represent the two-dimensional spatial coordinates of mounting post 110. In the exemplary embodiment of FIG. 1, spatial coordinated X4 and Y4 may be selected from an applicable range approximately spanning from 5.041 to 5.1 inches and 4.098 to 4.108 inches, respectively. In accordance to one exemplary embodiment, parameters X4 and Y4 may be set to an optimal value of approximately 5.046 and 4.103 inches, respectively. Parameters X5 and Y5, denoted in FIG. 1, represent the two-dimensional spatial coordinates of localization divot 112 disposed at the top portion 102 of the DRF 101. In the exemplary embodiment of FIG. 1, spatial coordinated X5 and Y5 may be selected from an applicable range approximately spanning from 3.852 to 3.862 inches and 3.730 to 3.740 inches, respectively. In accordance to one exemplary embodiment, parameters X5 and Y5 may be set to an optimal value of approximately 3.857 and 3.735 inches, respectively.

Disclosed embodiments of the DRF 101 may also provide localization divots 114 and 116 disposed at front portion 118 and back portion 120 of the DRF 101, respectively. Parameters X6 and Y6, denoted in FIG. 1, represent the two-dimensional spatial coordinates of localization divot 114 disposed at the front portion 118 of DRF 101. In the exemplary embodiment of FIG. 1, spatial coordinated X6 and Y6 may be selected from an applicable range approximately spanning from 2.538 to 2.549 inches and 4.052 to 4.062 inches, respectively. In accordance to one exemplary embodiment, parameters X6 and Y6 may be set to an optimal value of approximately 2.544 and 4.057 inches, respectively. Parameters X7 and Y7, denoted in FIG. 1, represent the two-dimensional spatial coordinates of localization divot 116 disposed at the back portion 120 of the DRF 101. In the exemplary embodiment of FIG. 1, spatial coordinated X7 and Y7 may be selected from an applicable range approximately spanning from 2.501 to 2.511 inches and 0.528 to 0.538 inches, respectively. In accordance to one exemplary embodiment, parameters X7 and Y7 may be set to an optimal value of approximately 2.506 and 0.533 inches, respectively. Parameter D1 represents the vertical distance between the top surface 122 of DRF 101 and center point of localization divot 114 disposed at the front portion 118 of the DRF 101 and denoted by two-dimensional spatial coordinates X6 and Y6 in FIG. 1. Parameter D2 represents the vertical distance between bottom surface 124 of DRF 101 and center point of localization divot 116 disposed at the back portion 120 of the DRF 101 and denoted by two-dimensional spatial coordinates X7 and Y7 in FIG. 1.

In some embodiments, DRF 101 may comprise an attachment portal which may be used to attach DRF 101 to a connection or a positioning member that may further be affixed to a patient's body part or to a surgical instrument. In FIG. 1, top surface region 116 and 118, with center coordinates X8, Y8 and X8, Y9 (of exemplary DRF 101) respectively correspond to an attachment portal and a mounting pin (for securing the DRF to an external frame) disposed at similar spatial coordinates on the bottom surface 124 (and illustrated further in FIG. 2). Attachment portal correspond to structure 126 in the back view and front view illustration of the exemplary DRF 101 in FIG. 1.

Basic geometry dictates that at least three coordinate points corresponding to three tracking marker elements are required to define a tracking marker reference plane (two-dimensional frame). However, preferably all four of the above mentioned tracking marker elements 107, 108, 109 and 110 should be inputted into the computer system to better define and correlate patient space with image space corresponding to pre-acquired radiological image.

Marker elements 106 may be designed as spherical marker elements including retro-reflective marker spheres, also referred to as passive reflective markers, and are widely used in image guidance systems. Embodiments of retro-reflective marker spheres may include those used to aid registration and instrument tracking during image guided surgery procedures such as neurological procedures, spine procedures and orthopedic procedures. Embodiments may include retro-reflective marker spheres having a high coefficient of retro-reflection on the external surface to provide feedback to the system/camera. Such surfaces may consist of micro glass spheres that reflect light. Depending on the medical application, different numbers and arrangements of retro-reflective marker spheres may be mounted on various types of surgical tools that may be used including that disclosed herein. Once mounted on a surgical probe, retro-reflective marker spheres provide an accurate reference point for the surgical probe in three-dimensional space.

Figure 2:
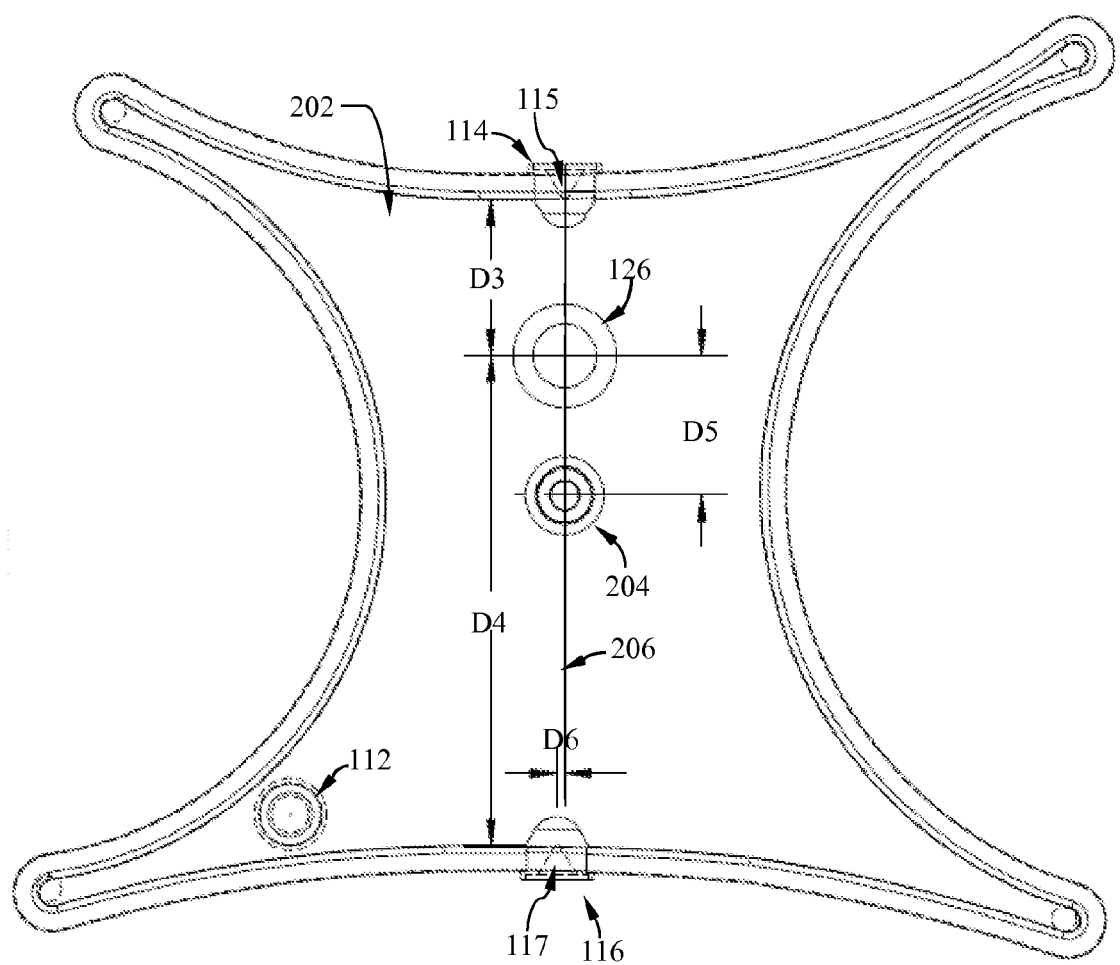
FIG. 2 illustrates a bottom view of the disposable dynamic reference frame of FIG. 1 utilized for a surgical navigation system, according to an embodiment of the present invention.

Turning to FIG. 2, device representation 200 illustrating top view of a bottom portion 202 of the exemplary DRF 101 and longitudinal cross-sectional view of the front portion and back portion localization divots 114 and 116, respectively as viewed from the bottom or top perspective view. Localization divots 114 and 116 may comprise a tapered recess portion 115 and 117, respectively for accommodating contact with, for example, a tip of a pointer probe. Parameters D3, D4 and D5, denoted in FIG. 1, represent the vertical offset of the front portion localization divot 114, back portion localization divot 116 and mounting pin 204 relative to the attachment portal 126. Front portion localization divot 114, attachment portal 126 and mounting pin 204 may have the same X coordinate value and thus lie at different points along a common vertical axis 206 in the plane of DRF 10. In the exemplary embodiment, the back portion localization divot 116 is horizontally offset from the vertical axis 206 by parameter D6. In the exemplary embodiment of FIG. 2, parameter D3, D4, D5 and D6 may be selected from an applicable range approximately spanning from 0.766 to 0.776 inches, 2.409 to 2.419 inches, 0.682 to 0.692 inches and 0.033 to 0.043 inches respectively. In accordance to one exemplary embodiment, parameters D3, D4, D5 and D6 may be set to an optimal value of approximately 0.771, 2.414, 0.687 and 0.038 inches, respectively.

Figure 3:
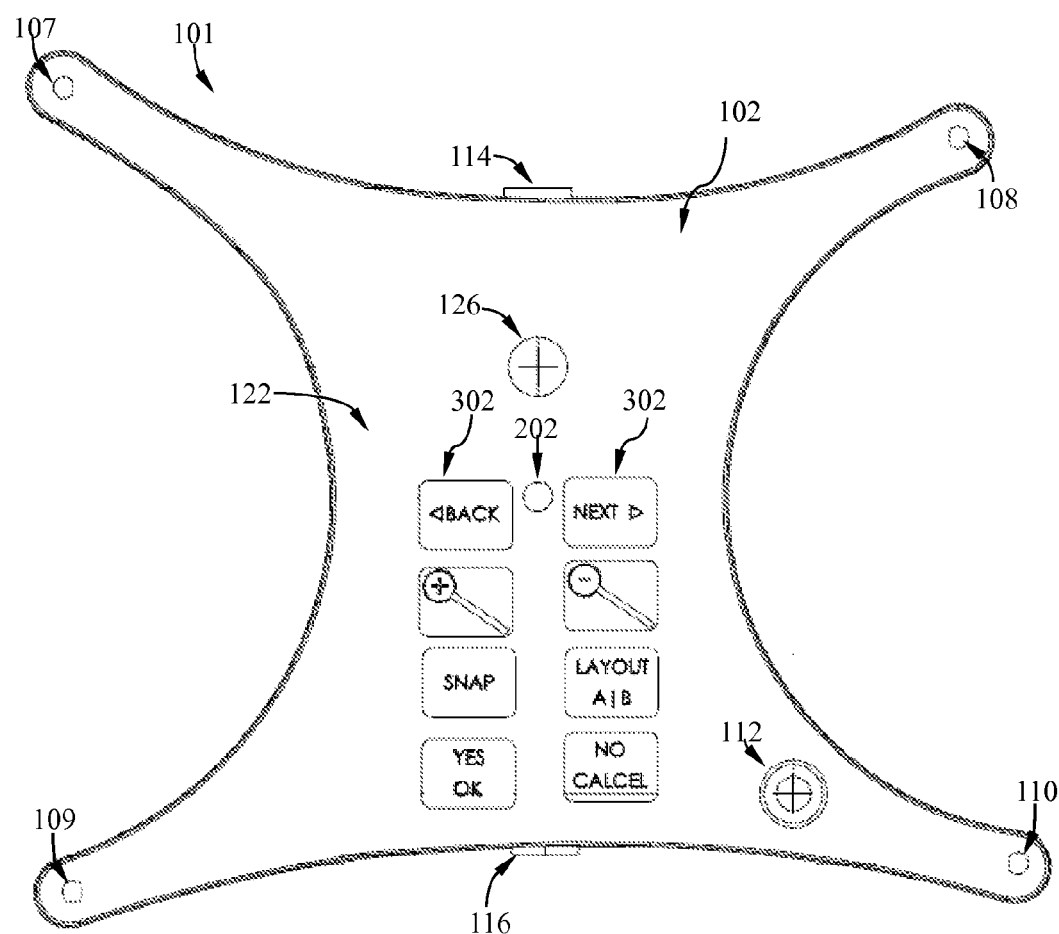
FIG. 3 illustrates a top view of the disposable dynamic reference frame highlighting a set of indicia disposed on the top surface of the device, according to one embodiment of the present invention.

Turning to FIG. 3, the trackable top portion 102 of DRF 101 may comprise a set of one or more indicia 302 corresponding to a plurality of functional icons, for example, on a touch screen or GUI display, wherein each functional icon represents an executable function. Conventionally executable functions of an electronic device, such as an imaging controller system, may be activated through a user interface (e.g., a keyboard, mouse, touch pen, touch screen or other suitable device) thus allowing a physician or user to provide inputs to control the imaging device. An added advantage of the disclosed DRF 101 having the set of one or more indicia 302 includes the fact that DRF 101 is managed conveniently at the location of the patient and is maintained as a sterile device.

In the described embodiment, physical locations associated with elements of DRF 101 may be registered to the image space locations which, in addition to the pre-acquired patient radiological image, may also comprise a plurality of functional icons graphically represented on the imaging display unit e. If the area enclosing a particular indicia 302 (e.g., disposed on the top surface 122 of DRF 101 in the patient space) is mapped onto the image display area associated with the corresponding graphically represented functional icons designated as part of the image space, then the executable function associated with a functional icon may be activated. For example, the executable function may be activated by invoking a software routine to execute the function associated with a functional icon. In one disclosed embodiment, this may occur in accordance with a vector of movement of the touched position on the top surface 122 of DRF 101, i.e., when a respective indicia is touched on the trackable top portion of the dynamic reference frame. This obviates the need to directly engage the computerized user interface which is typically disposed at a work station away from the operating table and, furthermore, may not be sterile. Examples of techniques that may be useful in spatially mapping physical objects to digital environments according to various embodiments of the present invention are described in U.S. patent application Ser. No. 09/250,267 to Maurer et al, entitled APPARATUS AND METHOD FOR REGISTERING OF IMAGES TO PHYSICAL SPACE USING A WEIGHTED COMBINATION OF POINTS AND SURFACES, filed Feb. 16, 1999, U.S. patent application Ser. No. 10/418,187 to Galloway et al, entitled METHOD AND APPARATUS FOR COLLECTING AND PROCESSING PHYSICAL SPACE DATA FOR USE WHILE PERFORMING IMAGE-GUIDED SURGERY, filed Apr. 16, 2003, and U.S. patent application Ser. No. 13/423,984 to Simon et al, entitled METHOD FOR REGISTERING A PHYSICAL SPACE TO IMAGE SPACE, filed Mar. 19, 2012, the entire contents and disclosures of which are incorporated herein by reference.

Figure 4:
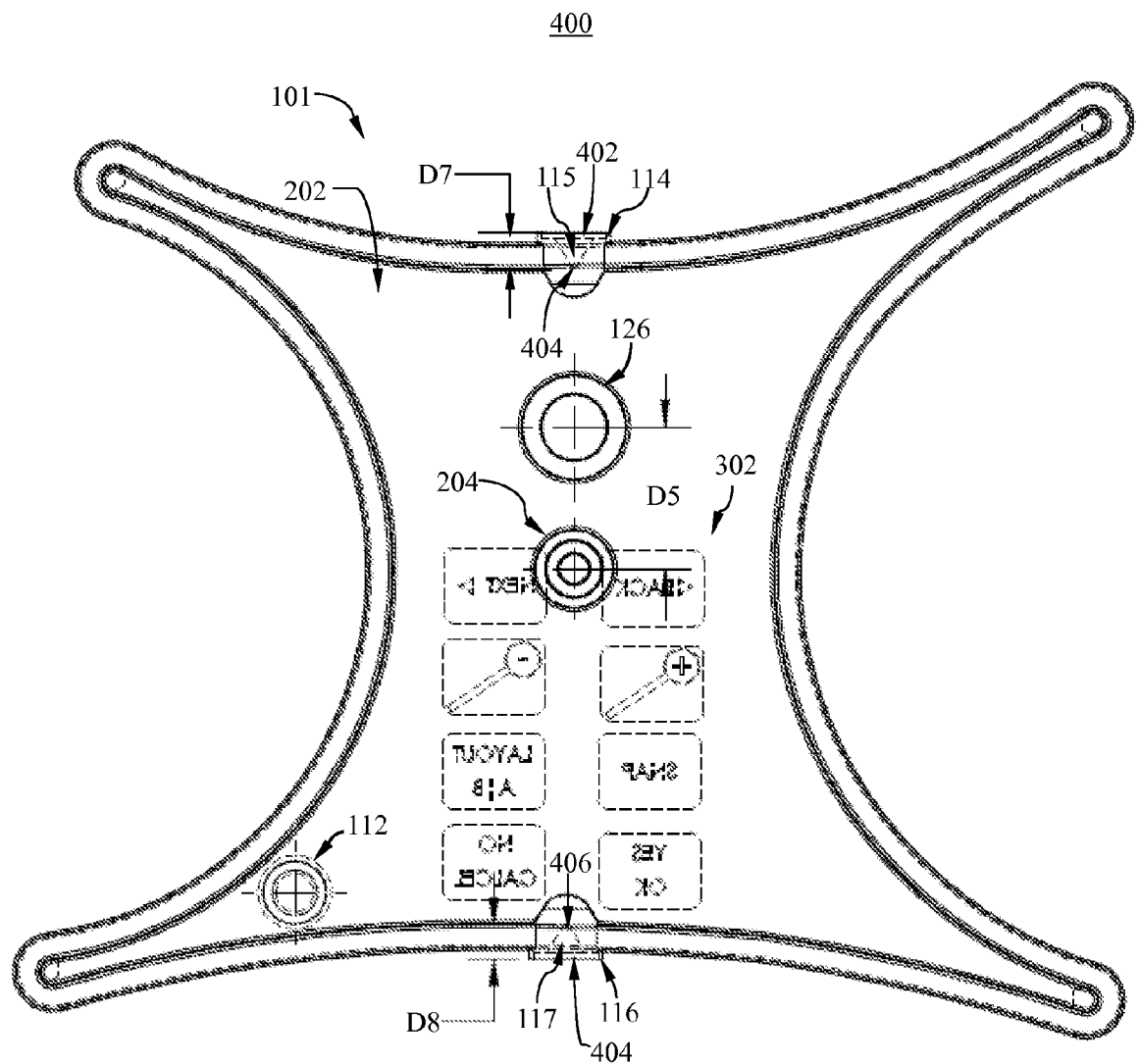
FIG. 4 illustrates a top view of the disposable dynamic reference frame highlighting the relative placement of the attachment portal and the mounting pin structure, according to an embodiment of the present invention.

FIG. 4 illustrates an exemplary placement of attachment portal 126 and the mounting pin 204 disposed on the back portion 202 of DRF 101 relative to indicia 302 disposed on the front portion 102 of the DRF 101. Parameter D7, denoted in FIG. 4, represents vertical separation between top surface 402 of the front portion localization divot 114 protruding beyond the plane of DRF 101 and an apex point 404 of the tapered recess portion 115 disposed in the front portion localization divot 114. Parameter D8, denoted in FIG. 4, represents vertical separation between top surface 405 of the back portion localization divot 116 protruding beyond the plane of DRF 101 and an apex point 406 of the tapered recess portion 117 disposed in the back portion localization divot 116. In the exemplary embodiment of FIG. 4, parameters D7 and D8 may be selected from an applicable range approximately spanning from 0.161 to 0.171 inches and 0.168 to 0.177 inches, respectively. In accordance to one exemplary embodiment, parameters D7 and D8 may be set to an optimal value of approximately 0.166 and 0.172 inches, respectively.

Figure 5:
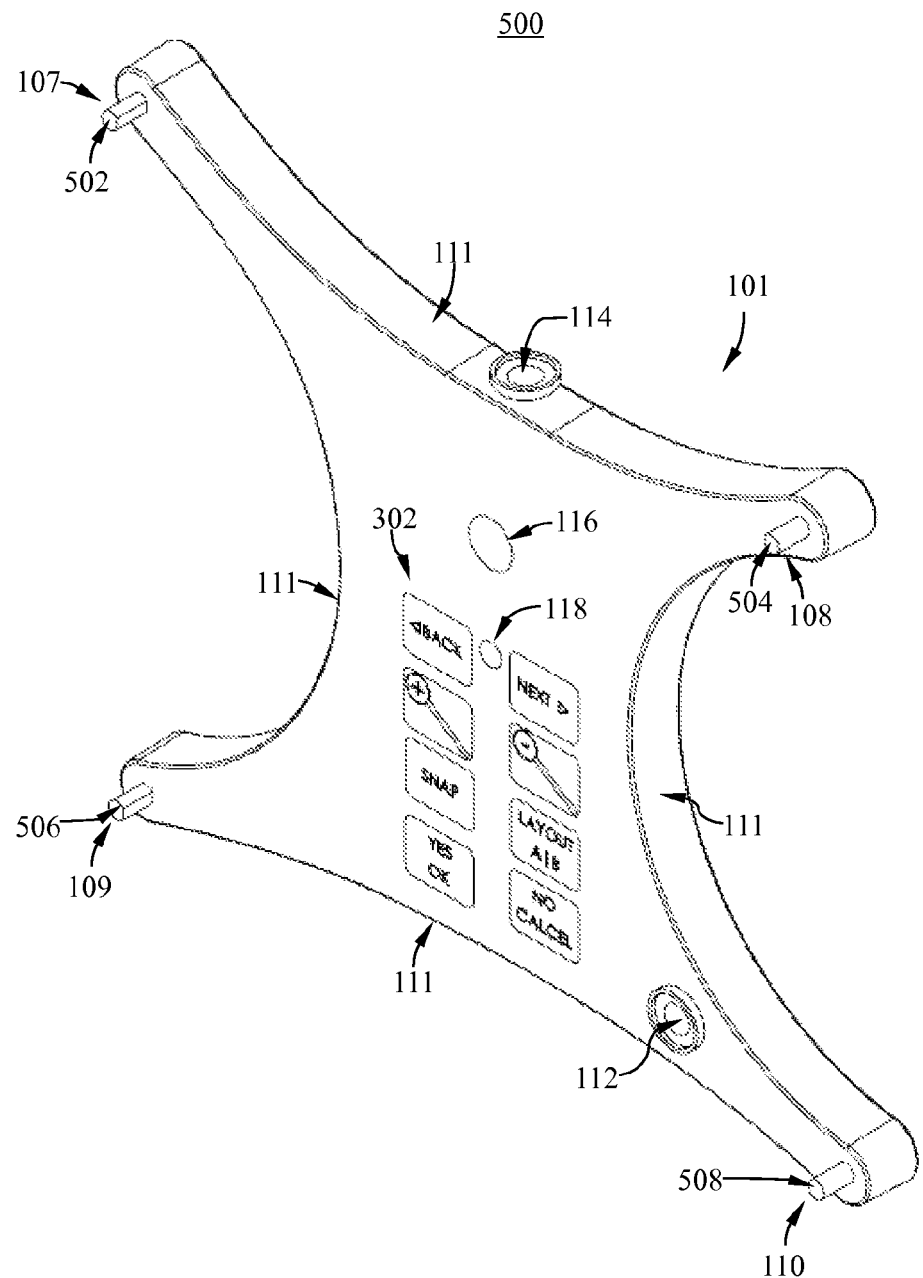
FIG. 5 is a perspective view of the disposable dynamic reference frame, according to one embodiment of the present invention.

FIG. 5 illustrates DRF 101 highlighting to top surface indicia, mounting post attachment locations of tracking marker elements and top portion and front portion localization divots. Accordingly, a perspective view of the exemplary DRF 101 depicts top portion 102, signifying mounting posts 107, 108, 109 and 110 for stable positioning of one or more tracking marker elements, remote activation indicia 302 and localization divots 112 and 114 (back portion localization divot 116 not shown). The geometrical shape of the DRF is designed with rigidity and stability of the frame structure to allow precise alignment of tracking marker elements. This is accomplished, inter alia, by providing enough supporting structure between mounting posts 107, 108, 109 and 110 (and, hence, the respectively mounted tracking marker elements) while still optimizing weight and manufacturing cost by reducing the amount of material used in construction through integration of one or more concave (inwardly-curved) sides 111 in the novel design of the DRF. To this extent, DRF 101 is manufactured to a sufficient rigidity to, thereby, inhibit planar misalignment of the top surface of mounting posts 107, 108, 109 and 110 (and, hence, the respectively mounted tracking marker elements, as further discussed below) through structural warping of the frame. In some disclosed embodiments, dynamic reference frame may be manufactured from plastic materials. For example, the manufacturing process may comprise molded plastic materials which allows reproducibility and accuracy in design.

In some preferred embodiments, the plastic comprises polycarbonate, polyetherimide (PEI) or another glass filled polymer such as polyetheretherketone (PEEK). A PEEK product description includes a high performance thermoplastic, unreinforced polyetheretherketone, semi crystalline, including granules for injection molding and extrusion, standard flow, FDA food contact compliant, color natural/beige. PEEK is applicable for applications for higher strength and stiffness as well as high ductility. It is chemically resistant to aggressive environments and suitable for sterilization for medical and food contact applications. PEEK property data table is provided as follows:

TABLE 1

|  | Nominal Value (English) | Nominal Value (SI) | Test Method |
|---|---|---|---|
| Physical | | | |
| Density | | | ISO 1183 |
| Crystalline | 1.30 g/cm³ | 1.30 g/cm³ | |
| Amorphous | 1.26 g/cm³ | 1.26 g/cm³ | |
| Mechanical | | | |
| Tensile Modulus (73° F. (23° C.)) | 537000 psi | 3700 Mpa | ISO 527-2 |
| Tensile Stress (Yield, | 14500 psi | 100 Mpa | ISO 527-2 |

TABLE 1-continued

| | Nominal Value (English) | Nominal Value (SI) | Test Method |
|---|---|---|---|
| 73° F. (23° C.)) | | | |
| Tensile Strain (Break, 73° F. (23° C.)) | 45% | 45% | ISO 527-2 |
| Flexural Strength | | | |
| 73° F. (23° C.) (at yield) | 23900 psi | 165 Mpa | |
| 3.5% Strain, 73° F. (23° C.) | 18100 psi | 125 Mpa | |
| 257° F. (125° C.) | 12300 psi | 85.0 Mpa | |
| 347° F. (175° C.) | 2610 psi | 18.0 Mpa | |
| 527° F. (275° C.) | 1890 psi | 13.0 MPa | |
| Compressive Stress | | | ISO 604 |
| 73° F. (23° C.) | 18100 psi | 125 Mpa | |
| 248° F. (120° C.) | 10200 psi | 70.0 Mpa | |
| Hardness | | | |
| Shore Hardness (Shore D, 73° F. (23° C.)) | 85 | 85 | ISO 868 |
| Thermal | | | |
| Heat Deflection Temperature | | | ISO 75-2/A |
| 264 psi (1.8 MPa), Unannealed | 306° F. | 152° C. | |
| Glass Transition Temperature | 289° F. | 143° C. | ISO 11357-2 |
| Melting Temperature | 649° F. | 343° C. | ISO 11357-3 |
| CLTE | | | |
| Flow: <289° F. (<143° C.) | 0.000025 in/in/° F. | 0.000045 cm/cm/° C. | |
| Flow: >289° F. (>143° C.) | 0.000067 in/in/° F. | 0.00012 cm/cm/° C. | |
| Transverse: | | | |
| <289° F. (<143° C.) | 0.000031 in/in/° F. | 0.000055 cm/cm/° C. | |
| >289° F. (>143° C.) | 0.000078 in/in/° F. | 0.00014 cm/cm/° C. | |
| Specific Heat (73° F. (23° C.)) | 0.526 Btu/lb/° F. | 2200 J/kg/° C. | DSC |
| Thermal Conductivity (73° F. (23° C.)) | 2.0 Bti-in/hr/ft$^2$/° F. | 0.29 W/m/K | ISO 22007-4 |
| Electrical | | | |
| Volume Resistivity | | | IEC 60093 |
| 73° F. (23° C.) | 1.0E+16 ohm · cm | 1.0E+16 ohm · cm | |
| 257° F. (125° C.) | 1.0E+15 ohm · cm | 1.0E+15 ohm · cm | |
| 437° F. (225° C.) | 1.0E+9 ohm · cm | 1.0E+9 ohm · cm | |
| Electric Strength | | | IEC 60093 |
| 0.00197 in (0.0500 mm) | 4800 V/mil | 190 kV/mm | |
| 0.0787 in (2.00 mm) | 580 V/mil | 23 kV/mm | |
| Dielectric Constant | | | |
| 73° F. (23° C.), 50 Hz | 3.00 | 3.00 | |
| 73° F. (23° C.), 1 kHz | 3.10 | 3.10 | |
| 257° F. (125° C.), 50 Hz | 4.50 | 4.50 | |
| Fill Analysis | | | ISO 11443 |
| Melt Viscosity (752° F. (400° C.)) | 350 Pa · s | 350 Pa · s | |
| Injection | | | |
| Drying Temperature | 248 to 302° F. | 120 to 150° C. | |
| Drying Time | 3.0 to 5.0 hr | 3.0 to 5.0 hr | |

A polycarbonate product description includes a glass and carbon fiber reinforced, mineral and process additive filled structural compound material. The polycarbonate product may be offered in all infinity base resins. The polycarbonate product provides improvements in strength, stiffness, creep resistance, fatigue endurance and impact and dimensional stability. Additional properties include increased thermal heat deflection temperature or heat distortion temperature (HDTUL) and long term heat resistance. Polycarbonate property data table is provided as follows:

TABLE 2

| | Nominal Value (English) | Nominal Value (SI) | Test Method |
|---|---|---|---|
| Physical | | | |
| Specific Gravity | 1.34 | 1.34 g/cm$^3$ | ASTM D792 |
| Specific Volume | 20.7 in$^3$/lb | 0.747 cm$^3$/g | |
| | | 1.26 g/cm$^3$ | |

TABLE 2-continued

|  | Nominal Value (English) | Nominal Value (SI) | Test Method |
|---|---|---|---|
| Mechanical | | | |
| Tensile Strength (Yield) | 16000 psi | 110 MPa | ASTM D638 |
| Tensile Elongation (Yield) | 2.0 to 4.0% | 2.0 to 4.0% i | ASTM D638 |
| Flexural Modulus | 1.00E+6 psi | 6890 MPa | ASTM D790 |
| Flexural Strength | 25000 psi | 172 Mpa | ASTM D790 |
| Thermal | | | |
| Deflection Temperature Under Load | | | ASTM D648 |
| 264 psi (1.8 MPa), Unannealed | 295° F. | 146° C. | |
| CLTE - Flow | 0.000015 in/in°/F. | 0.000027 cm/cm°/C. | ASTM D696 |
| Electrical | | | |
| Surface Resistivity | 1.0E+17 ohm | 1.0E+17 ohm | ASTM D257 |
| Injection | | | |
| Drying Temperature | 250° F. | 121° C. | |
| Drying Time | 4.0 hr | 4.0 hr | |
| Processing (Melt) Temp. | 540 to 630° F. | 282 to 332° C. | |
| Mold Temperature | 200° F. | 93.3° C. | |

Polyetherimide material (PEI) property data table is provided as follows:

TABLE 3

|  | English | SI Metric | ASTM TEST |
|---|---|---|---|
| Performance | | | |
| Specific Gravity | 1.27 | 1.27 | D 792 |
| Melt Flow Rate | | | |
| @337° C./6.6 kg | 17.80 g/10 min | 17.80 g/10 min | D 1238 |
| Molding Shrinkage | | | |
| ⅛ in (3.2 mm) section | 0.0050-0.0070 in/in | 0.50-0.70% | D 955 |
| Mechanical | | | |
| Tensile Strength | 16000 psi | 110 MPa | D 638 |
| Tensile Elongation | >10.0% | >10.0% | D 638 |
| Tensile Modulus | $0.52 \times 10^6$ psi | 3585 MPa | D 638 |
| Flexural Strength | 24000 psi | 165 MPa | D 790 |
| Flexural Modulus | $0.50 \times 10^6$ psi | 3448 MPa | D 790 |
| General Processing for Injection Molding | | | |
| Injection Pressure | 12000-18000 psi | 83-124 MPa | |
| Melt Temperature | 670-750° F. | 354-399° C. | |
| Mold Temperature | 275-350° F. | 135-177° C. | |
| Drying | 4 hrs @ 300° F. | 4 hrs @ 149° C. | |
| Moisture Content | 0.04% | 0.04% | |
| Dew Point | −20° F. | −20° C. | |

In an alternative embodiment, DRF 101 may comprise a rigid metal. The metal may comprise aluminum, anodized aluminum and stainless steel. For 6000 Series Aluminum Alloy; Aluminum Alloy; Metal; Nonferrous Metal, a property data table is provided as follows:

TABLE 4

| Component | Wt. % |
| --- | --- |
| Al | 95.8-98.6 |
| Cr | 0.04-0.35 |
| Cu | 0.15-0.4 |
| Fe | Max 0.7 |
| Mg | 0.8-1.2 |
| Mn | Max 0.15 |
| Other, each | Max 0.05 |
| Other total | Max 0.15 |
| Si | 0.4-0.8 |
| Ti | Max 0.15 |
| Zn | Max 0.25 |

TABLE 5

| | Metric | English |
| --- | --- | --- |
| Physical Properties | | |
| Density | 2.7 g/cc | 0.0975 lb/in$^3$ |
| Mechanical Properties | | |
| Hardness Brinell | 95 | 95 |
| Hardness Knoop | 120 | 120 |
| Hardness Rockwell A | 40 | 40 |
| Hardness Rockwell B | 60 | 60 |
| Hardness Vickers | 107 | 107 |
| Ultimate Tensile Strength | 310 Mpa | 45000 psi |
| Tensile Yield Strength | 276 MPA | 40000 psi |
| Modulus of Elasticity | 68.9 GPa | 10000 ksi |
| Poisson's Ratio | 0.33 | 0.33 |
| Fatigue Strength | 96.5 Mpa | 14000 psi |
| Shear Modulus | 26 GPa | 3770 ksi |
| Shear Strength | 207 Mpa | 30000 psi |
| Electrical Properties | | |
| Electrical Resistivity | 3.99e–066 ohm-cm | 3.99e–066 ohm-cm |

Tracking marker element 106 may be designed as spherical marker element including a retro-reflective marker sphere, also referred to as passive reflective marker. Embodiments of retro-reflective marker spheres may include those used to aid registration and instrument tracking during image guided surgery procedures such as neurological procedures, spine procedures and orthopedic procedures. Embodiments may include a retro-reflective marker sphere having a high coefficient of retro-reflection on the external surface to provide feedback to the system/camera. Such surfaces may consist of micro glass spheres that reflect light. Depending on the medical application, different numbers and arrangements of retro-reflective marker spheres may be mounted on various types of surgical tools that may be used including that disclosed herein. Once mounted on a surgical probe, retro-reflective marker spheres provide an accuracy reference point for the surgical probe in three-dimensional space.

Embodiments of marker element 106 may include internal structures for receiving and mating with mounting post 107, 108, 109 and 110. In the disclosed embodiment, internal structure may be designed to not only mount marker element 106 to mounting post 107. 108, 109 and 110, but ensure that marker element 106 is consistently and accurately mounted such that full alignment is maintained after mounting to dynamic frame reference 101.

For example, embodiments of the disclosed invention provide an internal stop surface of the tracking marker elements 106 that abut the top surfaces 502, 504, 506 and 508 of mounting post 107, 108, 109 and 110, respectively. As described earlier, the rigidity and the structural stability of DRF 101 inhibits planar misalignment of top surfaces 502, 504, 506 and 508 of mounting posts 107, 108, 109 and 110, respectively. Top surfaces 502, 504, 506 and 508 of mounting posts 107, 108, 109 and 110 are configured to align on a common horizontal plane that extends in parallel with top surface 122 of top portion 102 of DRF 101. The internal stop surface of tracking marker elements 106 may be mounted in abutment with top surfaces 502, 504, 506 and 508 of mounting post 107, 108, 109 and 110, respectively. By doing so, a centerline of tracking marker elements 106 may align on the same common horizontal plane that extends in parallel with the top portion 102 of DRF 101. The resultant coupling achieves precise inter-alignment of the one or more tracking marker elements 106 onto DRF 101.

Furthermore, embodiments of the disclosed invention provide that the materials and material characteristics described herein are well suited for DRF 101 to be utilized as a disposable single-use device being manufactured with tracking marker elements 106 pre-attached to the DRF during the manufacturing process. A sterile single-use disposable DRF of the disclosed invention may be packaged to maintain its sterile integrity and be made available and ready for use upon request. In some embodiments, a preferred design includes a design configuration wherein the setup of the pre-attached tracking marker elements 106 is ready for use such that the tracking marker elements 106 are correctly aligned along DRF 101.

It is noted that tracking marker elements 106 may be mounted to mounting post 107, 108, 109 and 110 by a user at the time of operation. Alternatively, tracking marker elements 106 may be pre-attached to mounting post 107, 108, 109 and 110 and ready for use for an operation. Thus, in an exemplary operation, when a surgeon opens a package containing the disclosed DRF 101, DRF 101 may be configured and employed within a surgical navigation system. Upon assembly, the unique design of the disclosed embodiment automatically and consistently aligns tracking marker elements 106 in alignment with suitable tolerance levels of the surgical navigation system requirements. Disclosed embodiments provide a carrier body for tracking marker elements defined by the two-dimensional plane of DRF 101 designed to correctly align and synch with the respective navigation system upon being integrated therein. The integration with the rest of the navigation system may occur, for example, via a mounting device coupled/mated with DRF 101 through the attachment portal 126. This facilitates enhancement of the setup efforts of the navigation system in a cost efficient manner and eliminates additional pre-registration and formatting procedures.

Having described the many embodiments of the present invention in detail, it will be apparent that modifications and variations are possible without departing from the scope of the present invention defined in the appended claims. For example, disclosed embodiments may provide certain indicia and/or colors on components of the disclosed disposable DRF device such as, but not limited to, attachment portal 126, mounting pin 204, top portion 102, bottom portion 202, front portion 118, back portion 120, concave (inwardly-curved) sides 111, mounting posts 107, 108, 109 and 110 and/or tracking marker elements 106. Such specific uses or applications associated with said indicia and/or colors may be employed, for example, in specific prescribed distinct surgical procedures or in certain environments or medical situations, or by specific groups of surgeons or individuals. These may include, but not limited to, for example, use in neuro and ENT surgery, spinal applications, soft/sensitive tissue applications and/or applying force applications. Additionally, other custom features may be employed and configured into the disclosed disposable DRF 101 such as pre-fashioned and custom made ergonomic grips/handles attachable to DRF 101. An example of a coloring scheme is presented as follows:

TABLE 6

| Color of Component (e.g., handle/grip) | Probe Name | Tip Specific |
|---|---|---|
| Orange | Blunt Pointer | Pointer used for Neuro and ENT use; tip is slightly rounded (R 0.25 mm). |
| Blue | Sharp Pointer | Pointer used for spinal application; tip is harp, so that anatomical landmarks on bones can be acquired. |
| Green | Ball Pin Pointer | Pointer for touching soft, sensitive tissue; tip with ball (R 1.5 mm). |
| Yellow | Extra Strong Pointer | Pointer for applying force, pointer tip with big diameter (R 2.5 mm). |

Furthermore, it should be appreciated that all examples in the present disclosure, while illustrating many embodiments of the present invention, are provided as non-limiting examples and are, therefore, not to be taken as limiting the various aspects so illustrated.

While the present invention has been disclosed with references to certain embodiments, numerous modifications, alterations, and changes to the described embodiments are possible without departing from the spirit and scope of the present invention, as defined in the appended claims. Accordingly, it is intended that the present invention not be limited to the described embodiments, but that it has the full scope defined by the language of the following claims, and equivalents thereof.

What is claimed is:

1. A device comprising:
a rigid frame member having a top portion;
a plurality of mounts each having a top surface, wherein the plurality of mounts are disposed at prescribed locations of the top portion;
wherein the top surface of the plurality of mounts are configured to align on a common horizontal plane that extends in parallel with the top portion of the frame member; and wherein indicia for respective functional icons are disposed on the top portion at respective prescribed locations registered to respective image space locations in an image space comprising radiological image data for a patient.

2. The device of claim 1, wherein a function is executed when the indicia representing the function is touched.

3. The device of claim 1, wherein the mounts comprise mounting posts.

4. The device of claim 3, wherein one or more tracking marker elements are mounted to the mounting posts such that upon mounting, a centerline of the one or more tracking marker elements align on the common horizontal plane that extends in parallel with the top portion of the frame member.

5. The device of claim 4, wherein the tracking marker elements are spherical.

6. The device of claim 4, wherein the tracking marker elements are light-reflecting spherical markers.

7. The device of claim 1, wherein the frame member comprises an asymmetrical configuration.

8. The device of claim 7, wherein the asymmetrical configuration comprises an astroid design rotated about a central normal axis of the frame member.

9. The device of claim 8, wherein a rotation angle is between 22 and 23 degrees.

10. The device of claim 8, wherein an external contour of the astroid design comprises concave (inwardly-curved) sides.

11. The device of claim 10, wherein the astroid design has four concave (inwardly-curved) sides.

12. The device of claim 10, wherein the concave (inwardly-curved) sides terminate at a cusp.

13. The device of claim 12, wherein the cusp comprises rounded corners.

14. The device of claim 12, wherein the mounts are disposed at each cusp.

15. The device of claim 1, wherein the device is disposable.

16. The device of claim 1, wherein the rigid frame is managed at a location of the patient.

17. The device of claim 16, wherein the device is maintained as a sterile device.

18. The device of claim 1, wherein the indicia corresponding to the respective functional icons includes a touch screen or a GUI display.

19. A method of manufacturing a device comprising:
connecting a plurality of mounts on a top surface of a frame member,
wherein each plurality of mounts has a top surface,
wherein the top surface of the plurality of mounts are configured to align on a common horizontal plane that extends in parallel with the top surface of the frame member;
mounting one or more tracking marker elements on each mount and aligning a centerline of each tracking marker element with the top surface; and
disposing indicia for respective functional icons at respective prescribed physical locations on the top surface of the frame member, wherein each of the respective prescribed physical locations is registered to a respective image space location corresponding to a respective functional icon disposed on a display unit configured to display patient radiological image data.

20. The method of claim 19, comprising executing a function associated with a functional icon by touching the respective indicia for the functional icon.

21. The method of claim 20, wherein executing the function associated with the functional icon comprises invoking an appropriate software routine.

22. The method of claim 19, wherein the frame member comprises an asymmetric configuration.

23. The method of claim 22, wherein the asymmetric configuration comprises an astroid design rotated about a central normal axis of the frame member.

24. The method of claim 23, wherein a rotation angle is between 22 and 23 degrees.

25. The method of claim 23, wherein an external contour of the astroid design comprises concave (inwardly-curved) sides.

26. The method of claim 25, wherein the astroid design has four concave (inwardly-curved) sides.

27. The method of claim 25, wherein the concave (inwardly-curved) sides terminate at a cusp.

28. The method of claim 27, wherein the cusp comprises rounded corners.

29. The method of claim 27, wherein the mounts are disposed at each cusp.

30. The method of claim 19, wherein mounting the one or more tracking marker elements on each mount and aligning a centerline of each tracking marker element with the top surface forms a pre-attached marker assembly on the device.

31. A device comprising:
a rigid frame member having a top portion; and
a plurality of mounts each having a top surface, wherein the plurality of mounts are disposed at prescribed locations of the top portion,
wherein the top surface of the plurality of mounts are configured to align on a common horizontal plane that extends in parallel with the top portion of the frame member,
wherein indicia corresponding to a plurality of functional icons are disposed on the top portion at respective prescribed locations, wherein each functional icon represents an executable function, said indicia registered to respective image space locations in an image space comprising radiological image data for a patient.

32. The device of claim 31, wherein the indicia corresponding to the plurality of functional icons includes a touch screen or a GUI display.

33. The device of claim 31, wherein the image space is disposed away from a location of the patient.

34. The device of claim 31, wherein the rigid frame is managed at a location of the patient.

35. The device of claim 34, wherein the device is maintained as a sterile device.

36. The device of claim 31, wherein an area enclosing particular indicia is mapped onto an image display area associated with a corresponding graphically represented functional icon designated as part of the image space.

37. The device of claim 36, wherein a software routine is invoked to execute the function associated with a functional icon.

\* \* \* \* \*